United States Patent [19]

Burton

[11] Patent Number: 5,228,851
[45] Date of Patent: Jul. 20, 1993

[54] SINGLE-USE DISPOSABLE PROPHYLACTIC ELASTIC SLEEVE

[76] Inventor: Clarence E. Burton, 1185 Dean St., Brooklyn, N.Y. 11216

[21] Appl. No.: 769,217

[22] Filed: Oct. 1, 1991

[51] Int. Cl.⁵ .................. A61C 1/16; B65D 85/14
[52] U.S. Cl. ........................ 433/116; 128/4; 206/69; 206/306; 206/363; 206/368; 604/171; 604/263
[58] Field of Search ............ 206/363, 368, 369, 306, 206/69; 433/116, 126; 604/163, 164, 171, 263; 128/4, 6

[56]         References Cited
           U.S. PATENT DOCUMENTS

| 1,539,253 | 5/1925 | Fuller .................. 433/116 |
| 3,136,417 | 6/1964 | Clinch .................. 206/69 X |
| 3,335,723 | 8/1967 | Waldman, Jr. .......... 604/163 X |
| 3,469,685 | 9/1969 | Baermann ............... 206/306 |
| 3,735,864 | 5/1973 | Eckhart ................. 206/489 |
| 4,515,592 | 5/1985 | Frankhouser ............ 604/163 |
| 4,551,137 | 11/1985 | Osborne ............... 604/171 |
| 4,741,326 | 5/1988 | Sidall et al. .......... 128/4 |
| 4,757,381 | 7/1988 | Cooper et al. ......... 206/369 X |
| 4,772,275 | 9/1988 | Erlich ................. 206/438 X |
| 4,869,238 | 9/1989 | Opie et al. ........... 128/6 |

Primary Examiner—Bryon P. Gehman

[57]         ABSTRACT

A one-use flexible elastic impervious protective sleeve adapted to be readily placed on a handle of a dental or medical instrument to prevent the transmission of bacteria from one patient to another. The sleeve is provided with finger engaging ring-shaped retention members to aid in placing and expanding the sleeve from a collapsed position over the handle to expose only the patient-engaging portion of the instrument. After use, the rings are utilized to remove the sleeve.

5 Claims, 2 Drawing Sheets

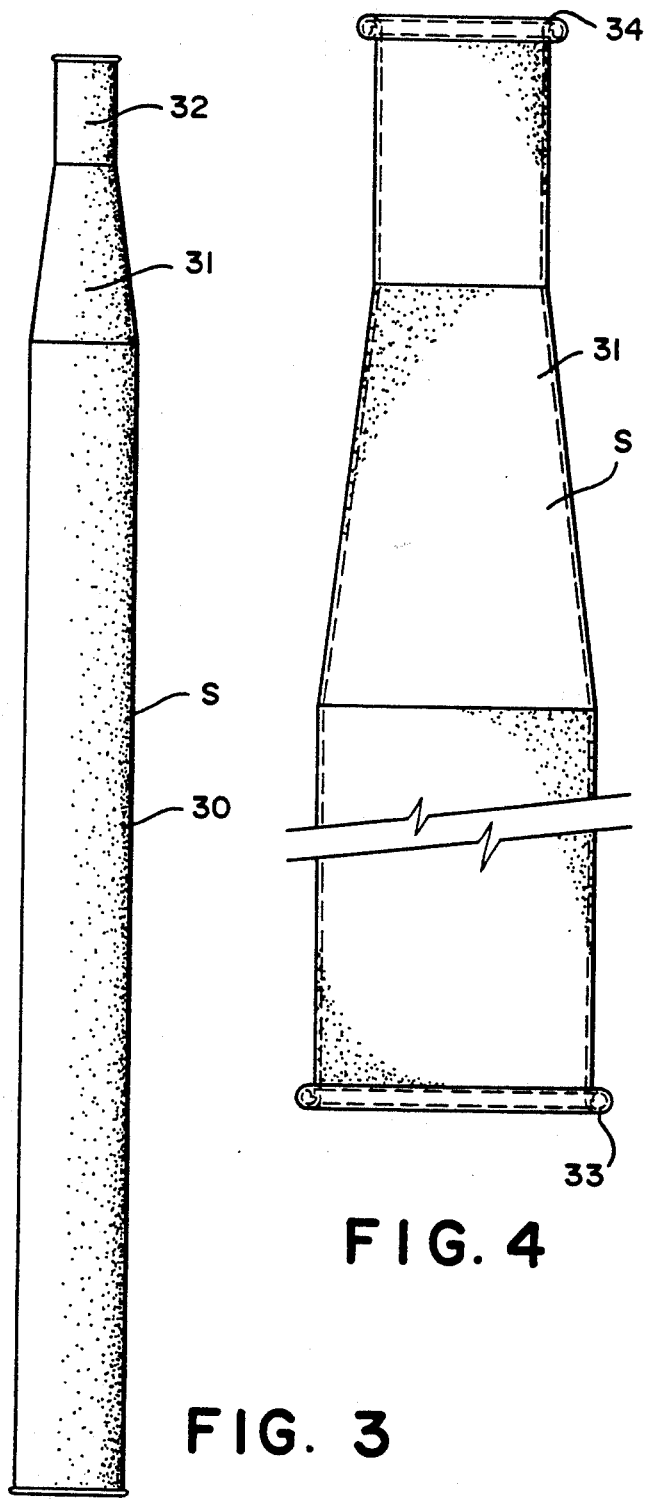
FIG. 3
FIG. 4
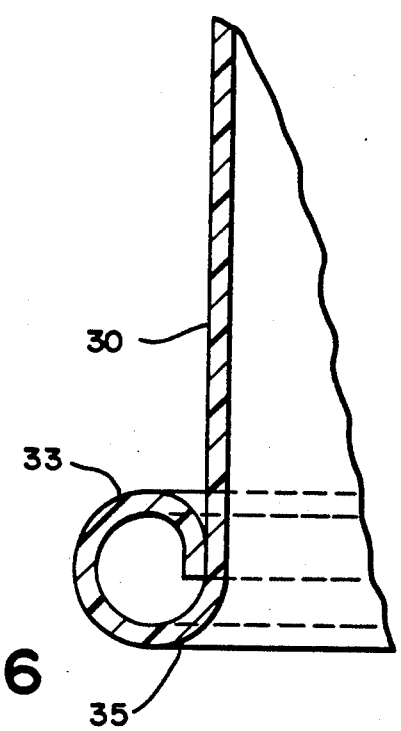
FIG. 5
FIG. 6

SINGLE-USE DISPOSABLE PROPHYLACTIC ELASTIC SLEEVE

FIELD OF THE INVENTION

The invention relates to a discardable sleeve of a specific construction designed to encase a medical/dental tool of the same general shape to prevent the transmission of germs from one patient to another.

BACKGROUND OF THE INVENTION

The majority of medical/dental patient type tools in prevalent use today have the characteristic that they are both connected to a source of power and will contact some part of the patients body. In the past, the reusable tools were sterilized between patients and many of the tools lend themselves to the various conventional sterilizing techniques. However, there are tools which do not fall into this category as a portion thereof, generally the handle, houses electrical components, wires, etc. and sterilizing the same is a time consuming and not very effective process.

The present invention is concerned with this latter type of tool and to this end a collapsible, flexible, thin, elastic, impervious sleeve has been designed to cover the same. The sleeve is intended to be discarded after each use to prevent patient-to-patient contact.

Protective sleeves of this nature are generally known and are classified in various subclasses in the Patent Office with the patents in Class 433, Sub 116 and Class 604, Subs 163 and 171 being particularly pertinent.

BRIEF DESCRIPTION OF THE DRAWINGS

FIG. 3 is a view of the protective sleeve in its extended use position;

FIG. 4 is a partial view of the sleeve of FIG. 3 showing the details of the end rings;

FIG. 5 is a top view of the sleeve in its collapsed stored position;

FIG. 6 is an enlarged partial section of the sleeve showing the details of the sleeve position.

DESCRIPTION OF THE PREFERRED EMBODIMENT

Figure 1:
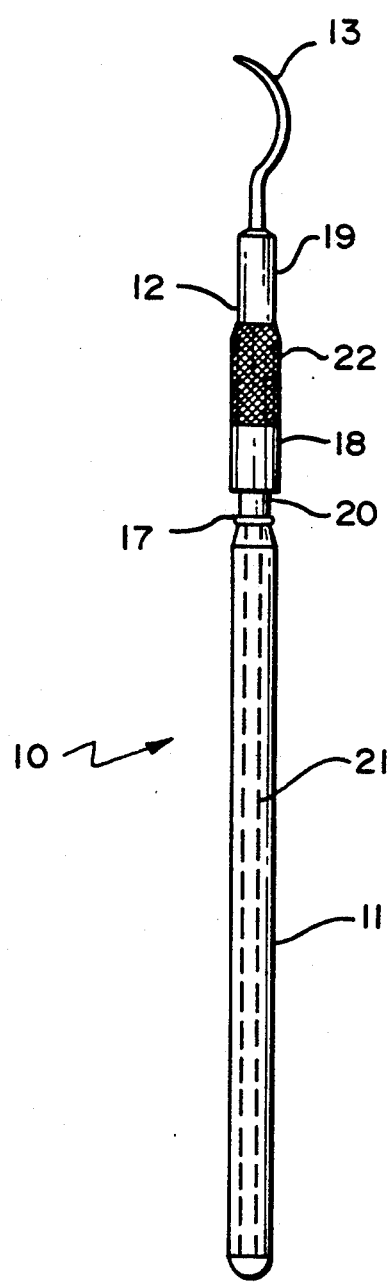
FIG. 1 is a perspective view of the tool that will be protected by the sleeve of the invention.
Figure 2:
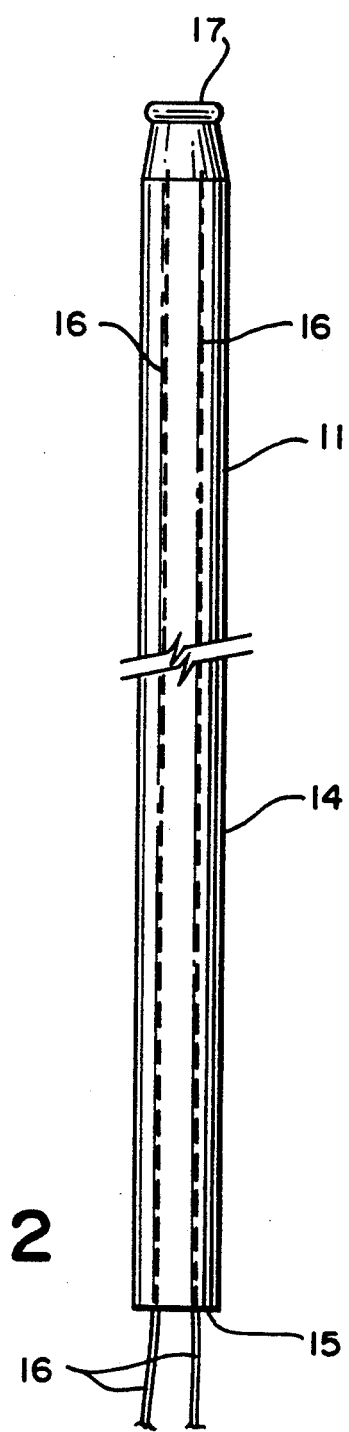
FIG. 2 is an enlarged detail view of the handle of the tool as disclosed in FIG. 1.

With reference to FIG. 1 of the drawing, the dental/medical tool to be protected is designated generally as 10 and typifies a well known shape as used in the trade and includes a main housing portion 11 and a removable tool supporting base 12 which in this instance supports a dental vibrating cleaning tool 13. As seen in FIG. 2, the main housing 11 comprises an elongated hollow member 14 of constant diameter having an opening 15 at one end to receive wires 16 from a power source, not shown, and an opposite collared open end 17 tapering down from the housing 11 to receive the tool supporting base 12.

Referring back to FIG. 1, the tool supporting base 12 is of a stepped configuration 18, 19 having a stem 20 supporting tool driving means 21 removable positioned within the housing 14 as shown in dotted outline and which cooperates with the wires 16 for driving the tool 13. Conventionally, the slipped portion 18 is knurled or grooved as at 22 to enhance the users grasping thereof between his thumb and forefinger while a portion of the housing 11 rests therebetween.

With the recent awareness of the problem of AIDs, sterilizing of dental/medical tools has become of the utmost importance and the sleeve of the present disclosure is designed to prevent the passing of germs from one patient to another by simply applying, removing and discarding the sleeve before and after each use. The sleeve is designed to cover the handle 14 of FIGS. 1 and 2 in as much as the same does not lend itself to be readily sterilized due to the electric wires 16 being disposed throughout the major portion of the same.

Presently, there is no effective way of sterilizing the same. The tool supporting base 12 and tool 13 can be readily sterilized by removing the same from the handle 14 and placed in a cleaning sterilizing solution as is well known and presents no problem of germ contact.

The sleeve S of the present invention is seen in FIGS. 3–6 inclusive, with FIG. 3 showing the same in its extended uncollapsed use position and is comprised of a tubular member prefereably made from latex. Latex is preferred as it is flexible, can be made thin and impervious, is economical and therefore disposable.

The sleeve S is comprised of a major elongated portion 30 having a substantially constant diameter which tapers down into a smaller section 31 which in turn has a further elongated section 32 of the same diameter as the smallest portion of section 31. As is readily apparent, when the sleeve S is placed on the tool, portion 30 will cover the handle 14, the tapering section 31 will cover the stepped configuration 18, 19 with the end section 32 terminating short of the tip 13, as shown in FIG. 1.

The sleeve S is further provided with rings 33, 34 formed at either end thereof, see FIGS. 4, 5 and 6, by rolling the free end 35 over on itself as shown in detail in FIG. 6 and held thereat by conventional manufacturing means.

FIG. 5 shows the sleeve S in its non-use stored collapsed position with the upper ring 34 disposed within the lower ring 33 and the remaining material gathered therewithin. Individual sleeve S can then be stored in a sterile housing prior to use. In using the same, the doctor or the like removes the collapsed sleeve from the sterile housing and using the ring 33 unrolls the same onto the to cover the base 12 and portions 18, 19 and 22 as seen in FIG. 1. Each of the rings 33, 34 serve to seal the base 12 from ingress of germs, etc.

I claim:

1. A disposable elastic sleeve snugly covering the tool-receiving portion on the end of an elongated handle of a dental or medical instrument, said sleeve being open at each end and being formed from a thin, flexible, impervious material, rings integrally formed with the sleeve at each end of said sleeve, the integral rings on each end of said sleeve respectively grasping both the elongated handle and the tool-receiving portion of the instrument, to thereby sealingly cover the elongated handle and tool-receiving portion of the instrument, whereby the sleeve is applied, removed and discarded before and after each use of the instrument, to thereby prevent the passing of germs from one patient to another.

2. The device of claim 1 wherein the sleeve is colored to provide a visible means of use to a patient.

3. The device of claim 1 wherein the sleeve is made from latex.

4. A disposable elastic sleeve according to claim 1, wherein before use the sleeve is in a collapsed condition wherein the sleeve is rolled back on itself to position one ring on one end of the sleeve within the other ring on the other end of the sleeve, said collapsed sleeve being stored in a sterile housing.

5. A disposable elastic sleeve according to claim 1, wherein the elongated handle of the instrument has a constant diameter section and a tapering section extending therefrom to the tool-receiving portion, said sleeve having a constant diameter portion and a tapering portion corresponding to the constant diameter and tapering section of the instrument handle and tool-receiving portion.

* * * * *